(12) United States Patent
Kazantsev et al.

(10) Patent No.: US 11,950,993 B2
(45) Date of Patent: Apr. 9, 2024

(54) SELF-EXPANDING MESH IMPLANT FOR ENDOSCOPIC HERNIOPLASTY

(71) Applicant: TITANIUM TEXTILES AG, Bentwisch (DE)

(72) Inventors: Anton Anatolevich Kazantsev, Ekaterinburg (RU); Ajrat Auhatovich Yusupov, Sverdlovsk Oblast (RU); Alexandr Ivanovich Alehin, Moscow (RU); Vladimir Andreevich Zavaruev, Moscow (RU)

(73) Assignee: TITANIUM TEXTILES AG, Bentwisch (DE)

( * ) Notice: Subject to any disclaimer, the term of this patent is extended or adjusted under 35 U.S.C. 154(b) by 923 days.

(21) Appl. No.: 16/966,663

(22) PCT Filed: Jan. 31, 2018

(86) PCT No.: PCT/RU2018/000048
§ 371 (c)(1),
(2) Date: Dec. 2, 2020

(87) PCT Pub. No.: WO2019/151885
PCT Pub. Date: Aug. 8, 2019

(65) Prior Publication Data
US 2021/0085832 A1    Mar. 25, 2021

(51) Int. Cl.
*A61F 2/00* (2006.01)
*A61L 31/02* (2006.01)
*A61L 31/08* (2006.01)

(52) U.S. Cl.
CPC .......... *A61F 2/0063* (2013.01); *A61L 31/022* (2013.01); *A61L 31/088* (2013.01); *A61F 2002/0068* (2013.01); *A61L 2430/34* (2013.01)

(58) Field of Classification Search
CPC ................. A61F 2/0063; A61F 2/0045; A61F 2002/0068; A61L 31/022; A61L 31/088; A61L 2430/34
See application file for complete search history.

(56) References Cited

U.S. PATENT DOCUMENTS 5,824,082 A * 10/1998 Brown ................. A61F 2/0063
                                                     623/11.11
5,888,201 A *  3/1999 Stinson ..................... A61F 2/90
                                                       606/198
(Continued)

FOREIGN PATENT DOCUMENTS

CN         204274719 U      4/2015
JP         2009095856 A     5/2009
(Continued)

OTHER PUBLICATIONS

English translation of the Written Opinion of the International Searching Authority dated Oct. 18, 2018 for corresponding International Application No. PCT/RU2018/000048, filed Jan. 31, 2018.

(Continued)

*Primary Examiner* — Katherine H Schwiker
(74) *Attorney, Agent, or Firm* — David D. Brush; Westman, Champlin & Koehler, P.A.

(57) ABSTRACT

In the field of medicine and medical technology, improving the technical properties of endoprostheses used for the surgical treatment of hernias. A self-expanding mesh endoprosthesis for endoscopic hernioplasty includes a mesh fabric made of threads and a self-expanding system incorporated in the mesh fabric, wherein the self-expanding system is made of polyfilament titanium threads located both in the structure and along the contour of the endoprosthesis, and wherein the titanium threads of the mesh fabric are made with a relief surface. The technical result increases efficiency of performing laparoscopic hernioplasty operations, increas- (Continued)

ing the plasticity, and reducing the risk of breakage of the threads in the mesh structure, simplifying the surgical technique for passing through and placement of the endoprosthesis, reducing the duration and trauma of surgery and, accordingly, accelerating the recovery of patients.

7 Claims, 3 Drawing Sheets

(56) References Cited

U.S. PATENT DOCUMENTS

| | | | |
|---|---|---|---|
| 6,319,264 B1 | 11/2001 | Tormala et al. | |
| 7,906,132 B2 | 3/2011 | Ziegler et al. | |
| 2006/0161256 A1* | 7/2006 | Ziegler | A61L 27/306 |
| | | | 427/2.24 |
| 2007/0087146 A1 | 4/2007 | Evans et al. | |
| 2009/0099409 A1* | 4/2009 | Luehrs | A61F 2/0045 |
| | | | 600/37 |
| 2016/0242889 A1* | 8/2016 | Brown | A61F 2/0063 |

FOREIGN PATENT DOCUMENTS

| | | |
|---|---|---|
| RU | 2199968 C2 | 3/2003 |
| RU | 121735 U1 * | 11/2012 |
| RU | 2551054 C1 | 5/2015 |
| RU | 2578359 C1 | 3/2016 |
| WO | 2007087146 A2 | 8/2007 |
| WO | 2015104014 A1 | 7/2015 |

OTHER PUBLICATIONS

Extended European Search Report dated Jul. 12, 2021 for parallel European Application No. 18903710.4.

International Search Report dated Oct. 11, 2018 for corresponding International Application No. PCT/ RU2018/000048, filed Jan. 31, 2018.

Written Opinion of the International Searching Authority dated Oct. 11, 2018 for corresponding International Application No. PCT/ RU2018/000048, filed Jan. 31, 2018.

Chinese Office Action dated Dec. 2, 2022 for corresponding Chinese Application No. 201880091173.5.

Bourauel Christoph et al, "Surface roughness of orthodontic wires via atomic force microscopy, laser specular reflectance, and profilometry", European Journal of Orthodontics, vol. 20, (Jan. 1, 1998), pp. 79-92.

Hryniewicz T et al, "Corrosion and surface characterization of titanium biomaterial after magnetoelectropolishing", Surface and Coatings Technology, Elsevier, NL, vol. 203, No. 10-11, doi:10. 1016/J.SURFCOAT.2008.11.028, ISSN 0257-8972, pp. 1508-1515, (Dec. 6, 2008).

Korean Office Action dated Feb. 21, 2022 for corresponding Korean Application No. 10 2020 7025090, filed Aug. 31, 2020.

English Translation of Chinese Office Action dated Dec. 2, 2022 for corresponding Chinese Application No. 201880091173.5.

* cited by examiner

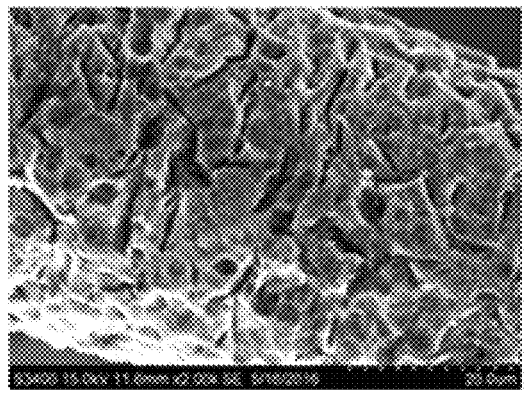
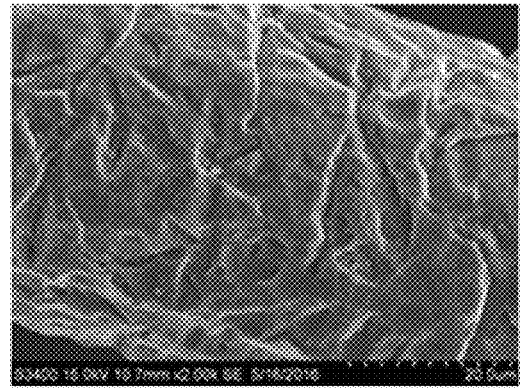
FIG. 6a FIG. 6b
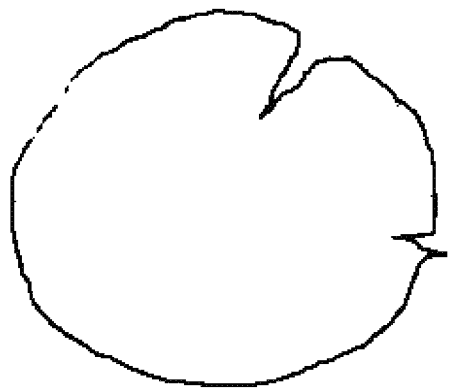
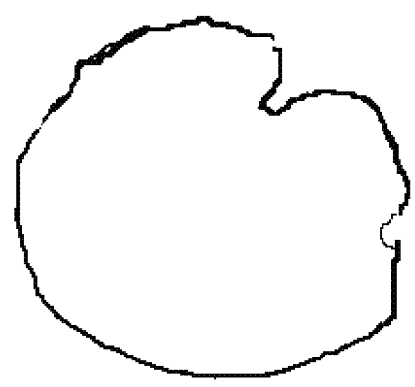
FIG. 7a FIG. 7b

SELF-EXPANDING MESH IMPLANT FOR ENDOSCOPIC HERNIOPLASTY

CROSS-REFERENCE TO RELATED APPLICATIONS

This Application is a Section 371 National Stage Application of International Application No. PCT/RU2018/000048, filed Jan. 31, 2018, which is incorporated by reference in its entirety and published as WO 2019/151885 A1 on Aug. 8, 2019, not in English.

FIELD OF THE INVENTION

The invention relates to the field of medicine and medical technology and is aimed at improving the technical properties of endoprostheses used for the surgical treatment of hernias.

STATE OF ART

A solution is known from the prior art (RU 2199968 C2, publ. Oct. 3, 2003, "Hernial orifice obturator"), which relates to the surgical technique and can be used for flexible coverage of defects of the anterior abdominal wall (hernial orifice, muscle diastasis). The obturator is made on the basis of a mesh implant made of titanium nickelide thread.

A disadvantage of this product is the use of titanium nickelide (NiTi) alloy as a base; when NiTi is implanted into the body, nickel diffusion into the surrounding tissues can take place. This metal in the form of Ni2+ ions has a pronounced toxic effect on the body cells. Various methods of NiTi surface treatment: (mechanical or electrochemical treatment, chemical etching), contribute to an increase in the corrosion resistance of the material, whereas the protective layer disruption increases the rate of nickel diffusion. The specified properties of titanium nickelide force it to be used with caution as a material for implants.

The Rebound HRD device (WO 2007087146 A2, publ. Feb. 8, 2007) should be considered as the closest analogue (prototype) with a full-fledged function of self-expanding. This device is a polypropylene, ultra-thin, lightweight macroporous mesh with a self-expanding wire frame made of titanium nickelide. The thickness of the nitinol wire is 2 to 2.5 mm. The mesh has a thread thickness of 250 µm and a surface density of 52 g/m$^2$, which places it in a class of light endoprostheses. Rebound HRDR meshes can be installed both laparoscopically or in open-cut operation through a small incision.

Disadvantages of Rebound HRD are that the mesh is based on a polypropylene structure, which has a lower biological stability. It should also be borne in mind that the implant is subject to cyclic loading, which causes metal fatigue when used. In this case, the use of the wire can cause a fracture of the material; nitinol string having a diameter of 2.0-2.5 mm can become a source of trauma or even perforation of nearby organs with the subsequent development of formidable complications. In addition, titanium nickelide during phase transitions can be a source of nickel release into the tissue. Said disadvantages reduce the efficiency of laparoscopic hernioplasty operations, increase the trauma rate and complicate the operative technique of passing through and placement the endoprosthesis, which negatively affects the acceleration of patient recovery.

The present invention makes it possible to substantially overcome said disadvantages inherent in the prototype.

DISCLOSURE OF THE INVENTION

The technical problem solved by the proposed technical solution is the development of a self-expanding endoprosthesis based on a titanium thread and reinforcing components for effective use during laparoscopic hernioplasty operations.

The technical result consists in increasing the efficiency of performing operations of laparoscopic hernioplasty, simplifying the surgical technique of passing through and placement of the endoprosthesis, increasing the plasticity, and reducing the risk of thread breakage, reducing the trauma and duration of surgery and, accordingly, accelerating the recovery of patients.

The technical result is achieved due to the fact that the self-expanding mesh endoprosthesis for endoscopic hernioplasty comprises a mesh fabric made of threads and a self-expanding system incorporated in the mesh fabric, wherein the self-expanding system is made of polyfilament titanium threads located both in the structure and along the contour of the endoprosthesis, and wherein the titanium threads of the mesh fabric are made with a relief surface.

Titanium threads of the self-expanding system are made of GRADE-5 alloy.

The relief of the surface of titanium thread of the mesh fabric is made with an uneven titanium thread diameter having fluctuations of from 0.00025 mm.

An oxide film is applied to the surface of relief titanium threads of the mesh fabric.

Polyfilament thread of the self-expanding system is made of monofilament threads with a diameter of 60-200 µm.

The diameter of polyfilament thread in the self-expanding system is no more than 600 µm.

Along the contour of the endoprosthesis, polyfilament titanium threads of the self-expanding system are enclosed in a shell of absorbable material.

BRIEF DESCRIPTION OF DRAWINGS

FIG. 6a. Example of relief of the thread surface after chemical etching;

FIG. 6b. Example of relief of the thread surface after ionic treatment;

FIG. 7a. Cross-section of the thread with longitudinal sharp-pointed defects before the treatment;

FIG. 7b. Cross-section of the thread with smoothed longitudinal defects after the treatment.

IMPLEMENTATION OF THE INVENTION

Figure 1:
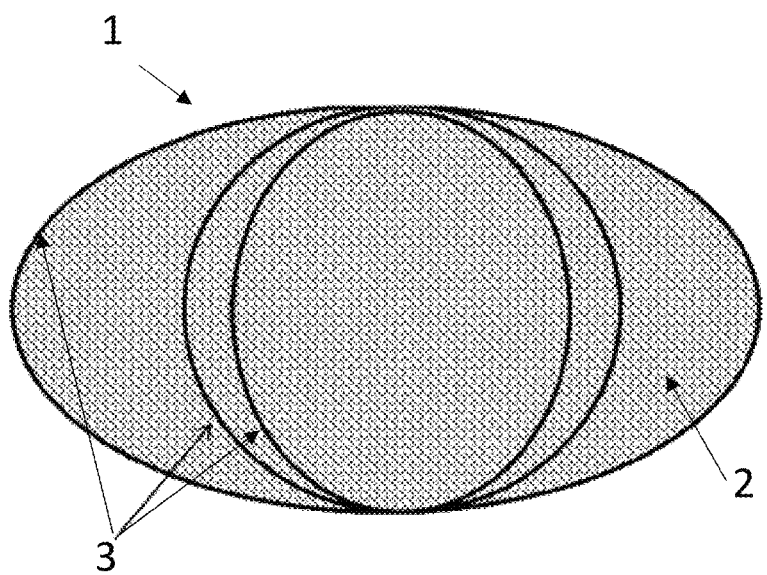
FIG. 1. Scheme of an endoprosthesis with a self-expanding system.
Figure 2:
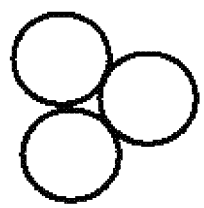
FIG. 2. Schematic representation of a cross-section of the polyfilament thread made of three monofilaments.
Figure 3:
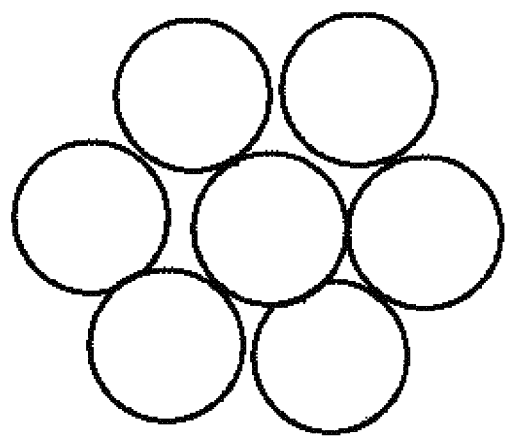
FIG. 3. Schematic representation of a cross-section of the polyfilament thread made of seven monofilaments.

The basis of the invention is a self-expanding system 3, consisting of polyfilament threads, enclosed in a mesh structure 2 of the endoprosthesis 1.

A polyfilament thread consists of several monofilament threads (monothreads), the number of which can range from 3 to 24. The diameter of the monofilament threads can be 60-200 μm, and the diameter of the entire polyfilament thread can reach 600 μm. The monofilament threads are made of GRADE-5 titanium alloy (Russian analogue of VT6). The spring properties of the used titanium threads from GRADE-5 alloys provide self-expanding and high elasticity of the expanding system 3.

The self-expanding system 3, consisting of the titanium polyfilament threads, is integrated into the structure of the mesh fabric 2. The titanium polyfilament threads of the system pass, intertwining through the mesh structure 2. The self-expanding system 3 provides the expanding of the material after it is rolled up for passing through the endoscope. The elasticity of the polyfilament thread can be varied in a wide range, which allows, on the one hand, to achieve resilience, and on the other hand, to avoid trauma of soft tissues.

The resilience can be varied when obtaining the material using a different amount of polyfilament thread and different structure thereof. For example, when polyfilament thread is made from three monofilament threads with a monofilament thread diameter of 60 μm, the pressure on soft tissues is minimal, while when polyfilament thread is made from seven monofilament threads with a monofilament thread diameter of 200 μm, the pressure on soft tissues is maximum. The more polyfilament threads are used in the self-expanding system, the more resilient is expansion thereof.

Optimal size for obtaining the resilient polyfilament thread is chosen empirically. When folded, a polyfilament thread thicker than 600 μm occupies more than 1.2 mm and occupies (in addition to the mesh) a significant space when passing through an endoscope having a diameter of 8-10 mm. Within such a range, the system has moderate resilience and does not exert excessive pressure on soft tissues.

A monofilament thread diameter less than 60 μm weakens the resilience of the polyfilament thread, generating an expanding force less than 3 N and do not allow full expanding of the mesh fabric. A diameter of more than 200 μm exerts an overpressure of more than 10 N, which affects the nearby tissues and may further cause discomfort to the patient. With a diameter of, for example, 130 μm, an expansion force of 6 N is generated, which is sufficient for expansion and does not create prerequisites for excessive pressure on the tissue.

Titanium polyfilament threads can be located both in the structure (central region) and along the contour (periphery) of the endoprosthesis 1, while their number, with a minimum diameter of a monofilament thread of 60 μm, can reach 49.

Along the periphery of the endoprosthesis 1, titanium polyfilament threads can be enclosed in a shell made of absorbable material, which excludes perforation of the delicate structures of the body with a monofilament thread. Lactic acid-based polymers such as polylactic acid, caprolactone and their isomers can be used as absorbable material.

Mesh fabric 2, which forms the basis of the self-expanding endoprosthesis, is made of filling-knit or warp-knitting metal fabric, which is made of monofilament or polyfilament titanium threads, for example, from GRADE-1 (analogue of VT1-00) titanium alloy. The mesh fabric is resistant to biological fluids; resistant to treatment cycles consisting of disinfection, pre-sterilization cleaning, and sterilization, has good biocompatibility with tissues, without causing toxic, allergic and other side reactions during implantation.

Figure 4A:
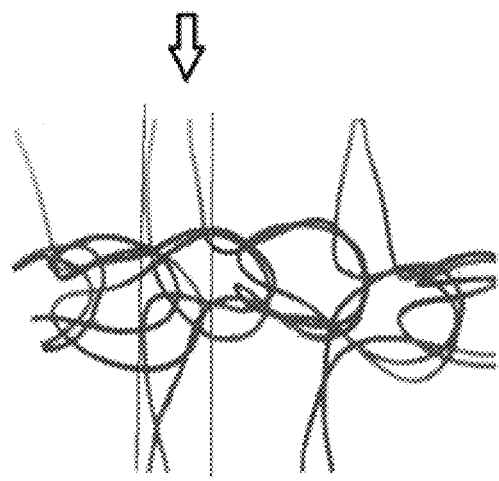
FIG. 4a. The state of the interloop range in the mesh fabric with relief threads.
Figure 4B:
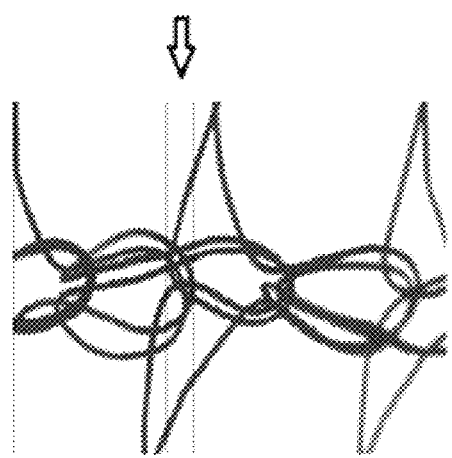
FIG. 4b. The state of the interloop range in the mesh fabric with threads without relief.

Titanium threads of the mesh fabric 2 are made with a relief surface obtained by, for example, power ultrasonic treatment, chemical etching, electrochemical polishing, ionic treatment, etc. These methods of treatment reduce the diameter of the titanium thread of the mesh fabric by 10-35% of the initial diameter, while reducing the area of interloop contacts. As a result, a "telescopic effect" is obtained: the penetration of loops and threads passing between loops into the area of adjacent loops, shown in FIG. 4a. This effect is not observed on the untreated thread (FIG. 4b). In FIGS. 4a and 4b, arrows and straight lines highlight the interpenetration of loops and threads passing between loops inside the loops in one looped column; the interpenetration in FIG. 4a is much greater.

The telescopic effect and reduction of resistance in the area of interloop contacts is the main factor in the elimination of "spring" properties. This fact is proved by measuring the mechanical properties of the material.

Figure 5:
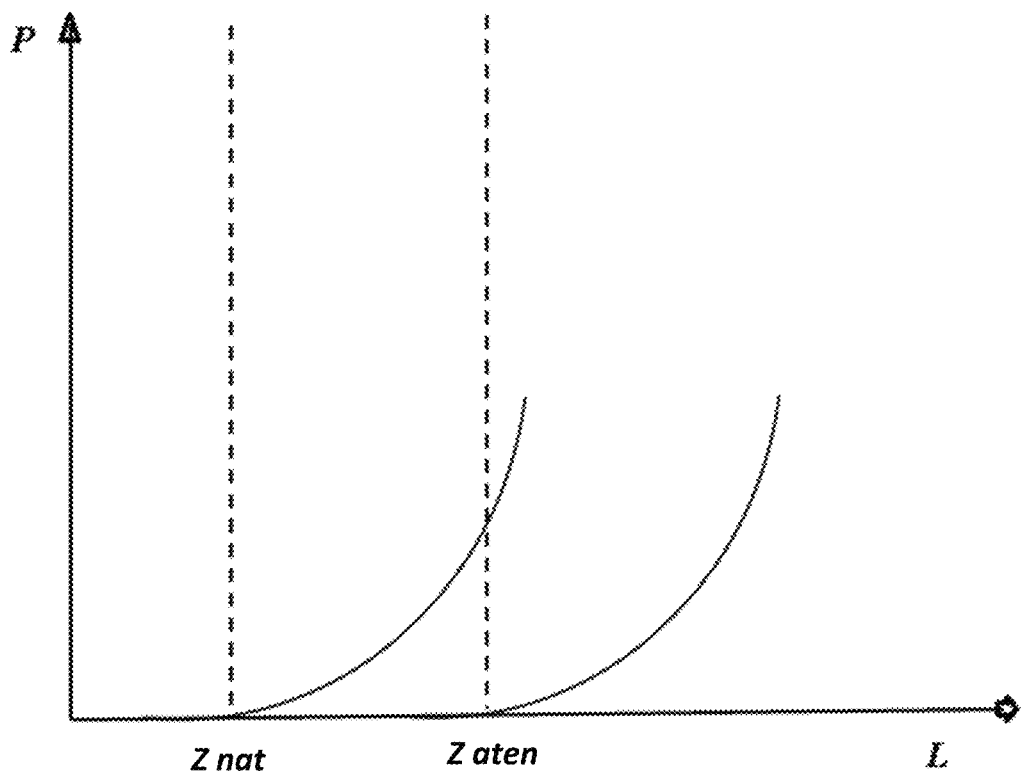
FIG. 5. Chart of zero tensile rigidity of knitted meshes.

Therefore, when stretching knitted meshes, there is a period of zero rigidity Z, where, $Z_{aten}$ is zero rigidity of the mesh fabric with relief threads (a tension knitted metal fabric), and $Z_{nat}$ is zero rigidity of the mesh fabric with threads without relief (native knitted metal fabric), i.e., the area on the diagram when the mesh fabric is stretched without resistance (FIG. 5). When comparing a conventional and treated mesh fabric of the same type of knitting and thread thickness, it is determined that the zone of zero rigidity of the treated mesh fabric made of relief threads is larger by 20% or more than that of an untreated mesh fabrics with threads without a relief.

As a result of technological processing, a relief appears on the surface of the titanium thread: chaotically located depressions and bumps (FIGS. 6a and 6b).

In addition, in the process of treatment on the surface of the thread located in the structure of the knitted mesh fabric, for example, by electrochemical polishing, longitudinal sharp-pointed defects (FIG. 7a) resulting from the drawing of the thread are smoothed. The smoothing of defects after the treatment is shown in FIG. 7b. Smoothed longitudinal defects, which are the concentrators of internal stress, harmonize the residual stress in the thread itself and reduce the risk of breakage of the mesh fabric.

A consequence of the treatment is also appearance of unevenness of the diameter of the titanium thread with fluctuations in length of from 0.00025 mm, which also creates additional freeness of interloop gaps.

To further increase the plasticity, an oxide film with a thickness of 1 to 3 μm having a low coefficient of sliding friction and allowing the loops to easily slide relative to each other, which positively affects the extensibility of the material, can be applied to the surface of the relief titanium threads of the mesh fabric. The surface oxide film reduces friction between knitted loops and the accompanying negative properties: breakage when expanding the material, etc. An oxide film is obtained by immersing the mesh fabric made of relief threads into a galvanic bath filled with the necessary solution, with a constant current, for a certain time. Depending on the time and the selected voltage, an oxide film with a thickness of 1-3 μm is formed on the surface of the titanium thread. In this case, the thickness of the thread itself does not increase.

The technology for using the endoprosthesis 1 is as follows: under general anesthesia, conductive tubes (trocars) are inserted through the skin incision of the anterior abdominal wall into the abdominal cavity of the patient, and then endoscopic instruments are inserted through them. A self-expanding titanium mesh endoprosthesis 1 rolled in the form of a cylinder is supposed to be inserted through a 10 mm trocar into the abdominal cavity. With slight traction of the edges of the endoprosthesis 1 with instruments, it expands (opens) in the operating field, closing the hernial defect. At the same time, an important feature of the endoprosthesis 1 is that its edges on the one side reach the edges of the wound; on the other hand, they do not exert too much pressure thereon.

The endoprosthesis 1 is placed on the area of the hernial defect, overlapping its edges by 3-5 centimeters. When stretching, the elastic edges of the mesh 2 abut on and self-fix a little in the wound. Due to the self-fixation, the endoprosthesis 1 is retained on the tissues without displacement, which facilitates its further fixation. Further fixation of the endoprosthesis 1 is performed using interrupted sutures or a herniostepler; in some cases, the endoprosthesis 1 does not require additional fixation. At the time of the completion of the operation, the endoprosthesis 1 is located in the anatomical region, closing the hernia orifice. Due to the fact that its edges abut against the boundaries of the operating field, the endoprosthesis 1 is additionally fixed in the operating field.

After the control of the operating wound state, instruments and trocars are removed from the abdominal cavity. Skin wounds of the anterior abdominal wall are sutured. An additional positive feature is the property of radiopacity of the titanium thread, which allows visualizing the location of the endoprosthesis 1 throughout the patient's life after surgery.

The high plasticity of the mesh fabric minimizes the spring properties, reduces the likelihood of biomechanical conflict between the tissue and the mucous membrane, and makes it possible to place the material under the mucous membrane without the risk of injury thereof. The mesh endoprosthesis freely expands over the surface of the surgical wound, easily assumes and maintains a given shape, and, is modeled according to the shape of the surgical wound by stretching, if necessary.

High porosity increases the rate of penetration of biological fluids into the endoprosthesis, accelerates the process of its colonization with fibroblasts and osteoblasts, and improves the biological integration of the material.

The mesh fabric made of titanium threads with a relief surface, being in contact with the wound surface, is instantly saturated with blood and wound discharge and exhibits pronounced adhesion to the wound surface, providing temporary self-fixation, allowing the surgeon to avoid using additional fixing elements. High adhesion to the wound surface makes it possible to place the titanium mesh on the tissues underlying or covering the endoprosthesis without tension, preventing such a frequent complication as surgical wound dehiscence.

At the same time, the highly porous structure does not retain the wound discharge, excluding the possibility of fluid leaks and further infection thereof.

The relief of the thread surface significantly improves the fixation of fibrin fibers thereon, thereby facilitating the attraction of fibroblasts serving as a source of newly formed connective tissue.

In contrast to analogues, when using the claimed endoprosthesis, the surgeon needs to perform a smaller incision, less actions and time for placing and straightening the endoprosthesis, thereby reducing the trauma and duration of surgery. It also requires less suture material and fewer internal sutures, less time for surgical wound to remain opened, less chance and less extent of microbial contamination. As a result, also: less duration of anesthesia, less risk of thromboembolic complications and negative impact of drugs.

Example 1

A model of a ventral hernia of the outer side of the anterior abdominal wall was obtained in three laboratory animals (rabbits, 4 months); a mesh endoprosthesis containing a system of expansion of 3 polyfilament threads made of a titanium alloy, each consisting of three monofilament threads with a monofilament thread diameter of 60 µm, was installed through the endoscope. Postoperative wound healing by primary intention. After 1 month, the animals were withdrawn from the experiment. When studying morphological changes, a whitish scar was found over the entire surface of the mesh endoprosthesis; upon microscopic examination, the structure of the postoperative scar was represented by ordered connective tissue fibers without signs of aseptic inflammation.

Example 2

A model of an umbilical hernia of the outer side of the anterior abdominal wall was obtained in three laboratory animals (rabbits, 4 months); a mesh endoprosthesis comprising a system of expanding of 7 polyfilament threads made of titanium alloy, each consisting of three monofilament threads with a monofilament thread diameter of 70 µm, was installed through the endoscope. Postoperative wound healing by primary intention. After 2 months, the animals were withdrawn from the experiment. When studying morphological changes: a whitish scar was found over the entire surface of the mesh endoprosthesis; upon microscopic examination, the structure of the postoperative scar was represented by ordered connective tissue fibers without signs of aseptic inflammation.

The claimed endoprosthesis, containing a self-expanding system made of polyfilament titanium threads located both in the structure and along the contour of the endoprosthesis in its mesh structure, as well as making the mesh structure threads in relief, makes it possible to increase the efficiency of laparoscopic hernioplasty operations, to increase plasticity and reduce the risk of breakage of the threads in the mesh structure, to simplify the surgical technique of passing through and placing the endoprosthesis, to reduce the trauma and duration of surgery, which leads to a speedy recovery of patients.

We claim:
1. A self-expanding mesh endoprosthesis for endoscopic hernioplasty, comprising:
    a mesh fabric made of titanium threads; and
    a self-expanding system enclosed in the mesh fabric, wherein the self-expanding system is made of one or more polyfilament titanium threads located both in a structure and along a contour of the endoprosthesis, and wherein the titanium threads of the mesh fabric are made with a relief surface.
2. The self-expanding mesh endoprosthesis for endoscopic hernioplasty according to claim 1, wherein the one or more polyfilament titanium threads of the self-expanding system are made of GRADE-5 alloy.
3. The self-expanding mesh endoprosthesis for endoscopic hernioplasty according to claim 1, wherein the relief surface of the titanium threads of the mesh fabric is made with an uneven diameter of the titanium thread of the mesh fabric having fluctuations of at least 0.00025 mm.
4. The self-expanding mesh endoprosthesis for endoscopic hernioplasty according to claim 1, further comprising an oxide film applied to the relief surface of the titanium threads of the mesh fabric.
5. The self-expanding mesh endoprosthesis for endoscopic hernioplasty according to claim 1, wherein the one or more polyfilament titanium threads of the self-expanding system are made of monofilament threads with a diameter of 60-200 lam.

6. The self-expanding mesh endoprosthesis for endoscopic hernioplasty according to claim 1, wherein the diameter of the one or more polyfilament titanium threads of the self-expanding system is not more than 600 μm.

7. The self-expanding mesh endoprosthesis for endoscopic hernioplasty according to claim 1, wherein the one or more polyfilament titanium threads of the self-expanding system along the endoprosthesis contour are enclosed in a shell of absorbable material.

\* \* \* \* \*